United States Patent
Yu et al.

(10) Patent No.: US 9,352,054 B2
(45) Date of Patent: *May 31, 2016

(54) METHOD AND APPARATUS FOR KIDNEY FUNCTION ANALYSIS

(71) Applicant: Indiana University Research and Technology Corporation, Indianapolis, IN (US)

(72) Inventors: Weiming Yu, Indianapolis, IN (US); Bruce A. Molitoris, Indianapolis, IN (US); Ruben M. Sandoval, Indianapolis, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 35 days.

This patent is subject to a terminal disclaimer.

(21) Appl. No.: 14/253,949

(22) Filed: Apr. 16, 2014

(65) Prior Publication Data

US 2014/0227189 A1 Aug. 14, 2014

Related U.S. Application Data

(62) Division of application No. 13/709,242, filed on Dec. 10, 2012, now Pat. No. 8,741,263, which is a division of application No. 11/911,895, filed as application No. PCT/US2006/014576 on Apr. 18, 2006, now Pat. No. 8,329,143.

(60) Provisional application No. 60/672,708, filed on Apr. 19, 2005.

(51) Int. Cl.
*A61K 49/00* (2006.01)

(52) U.S. Cl.
CPC ......... *A61K 49/0004* (2013.01); *A61K 49/0032* (2013.01); *A61K 49/0041* (2013.01); *A61K 49/0054* (2013.01)

(58) Field of Classification Search
CPC ........... A61K 49/0032; A61K 49/0004; A61K 49/0054
See application file for complete search history.

(56) References Cited

U.S. PATENT DOCUMENTS

| | | | |
|---|---|---|---|
| 5,928,625 A | 7/1999 | Dorshow et al. | |
| 8,329,143 B2 | 12/2012 | Yu et al. | |
| 2005/0136002 A1 | 6/2005 | Fossheim et al. | |
| 2013/0101518 A1 | 4/2013 | Yu et al. | |

FOREIGN PATENT DOCUMENTS

| | | |
|---|---|---|
| JP | 2005-237755 | 9/2005 |
| WO | 01/66152 | 9/2001 |

OTHER PUBLICATIONS

Annet, L., L. Hermoye, F. Peeters, F. Jamar, J. P. Dehoux and B. E. Van Beers, "Glomerular Filtration Rate: Assessment with Dynamic Contrast-Enhanced MRI and a Cortical-Compartment Model in the Rabbit Kidney", J. Magn Reson Imaging, vol. 20, No. 5, 2004, pp. 843-849.

Brewer, B. D., S. F. Clement, W. S. Lotz and R. Gronwall, "Single Injection Inulin/PAH Method for the Determination of Renal Clearances in Adult Horses and Ponies", J Vet Pharmacol Ther, vol. 11, No. 4, 1988, pp. 409-412.

Buonocore, M. H. and R. W. Katzberg, "Estimation of Extraction Fraction (EF) and Glomerular Filtration Rate (GFR) Using MRI: Considerations Derived from a New Gd-Chelate Biodistribution Model Simulation", IEEE Trans Med Imaging, vol. 24 No. 5, 2005, pp. 651-666.

Cousins, C., R. D. Gunasekera, M. Mubashar, S. Mohammadtaghi, R. Strong, M. J. Myers and A. M. Peters, "Comparative Kinetics of Microvascular Inulin and 99mTc-Labelled Diethylenetriaminepenta-acetic Acid Exchange", Clin Sci (Lond), vol. 93, No. 5, 1997, pp. 471-477.

Cousins, C., S. Mohammadtaghi, M. Mubashar, R. Strong, R. D. Gunasekera, M. J. Myers and A. M. Peters, "Clearance Kinetics of Solutes Used to Measure Glomerular Filtration Rate", Nucl Med Commun, vol. 20, No. 11, 1999, pp. 1047-1054.

Dagher, P. C., S. Herget-Rosenthal, S. G. Ruehm, S. K. Jo, R. A. Star, R. Agrawal and B. A. Molitoris, "Newly Developed Techniques to Study and Diagnose Acute Renal Failure", J Am Soc Nephrol, vol. 14, No. 8, 2003, pp. 2188-2198.

Dunn, Kenneth W. et al., Functional Studies of the Kidney of Living Animals Using Multicolor Two-photon Microscopy, American Journal of Physiology—Cell Physiology, Sep. 2002, pp. C905-C916, vol. 283, No. 3.

Erley, Christiane M. et al., Plasma Clearance of Iodine Contrast Media as a Measure of Glomerular Filtration Rate in Critically Ill Patients, Critical Care Medicine, Aug. 2001, pp. 1544-1550, vol. 29, No. 8.

Filler, G., A. Bokenkamp, W. Hofmann, T. Le Bricon, C. Martinez-Bru and A. Grubb, "Cystatin C as a Marker of GFR—History, Indications, and Future Research", Clin Biochem, vol. 38, No. 1, 2005, pp. 1-8.

Fischer, P. A., C. B. Bogoliuk, A. J. Ramirez, R. A. Sanchez and L. D. Masnatta, "A New Procedure for Evaluation of Renal Function Without Urine Connection in Rat", Kidney Int, vol. 58, No. 3, 2000, pp. 1336-1341.

Greenblatt, D. J. and J. Koch-Weser, "Clinical Pharmacokinetics (first of two Parts)", N. Engl. J. Med., vol. 293, No. 14, 1975, pp. 702-705.

Greenblatt, D. J. and J. Koch-Weser, "Clinical Pharmacokinetics (second of two Parts)", N. Engl. J. Med., vol. 293, No. 19, 1975, pp. 964-970.

(Continued)

*Primary Examiner* — Zohreh Fay
(74) *Attorney, Agent, or Firm* — Barnes & Thornburg LLP (57) ABSTRACT

A method and apparatus for determining physiological data related to an animal, such as kidney diagnostics data, is provided. The method includes injecting a mixture of a first and a second molecule into an animal (e.g., a human patient), determining a molecular ratio of the molecules, and determining the physiological data based on the molecular ratio. The apparatus includes a number of finger receiving apertures, a light generation circuit, a light detection circuit, a pulse counting circuit, and a user interface.

20 Claims, 6 Drawing Sheets

(56) References Cited

OTHER PUBLICATIONS

Haller, M., K. Rohner, W. Muller, F. Reutter, H. Binder, W. Estelberger and P. Arnold, "Single-Injection Inulin Clearance for Routine Measurement of Glomerular Filtration Rate in Cats", J. Feline Med Surg, vol. 5, No. 3, 2003, pp. 175-181.

Lorenz, J. N. and E. Gruenstein, "A Simple, Nonradioactive Method for Evaluating Single-Nephron Filtration Rate Using FITC-Inulin", Am J Physiol, vol. 276, 1 Pt 2, 1999, pp. F172-F177.

Meucci, V., A. Gasperini, G. Soldani, G. Guidi and M. Giorgi "A New HPLC Method to Determine Glomerular Filtration rate and Effective Renal Plasma Flow in Conscious Dogs by Single Intravenous Administration of Iohexol and P-Aminohippuric Acid", J. Chromatogr Sci, vol. 42, No. 2, 2004, pp. 107-111.

Molitoris, Bruce A., Intravital Multiphoton Microscopy of Dynamic Renal Processes, American Journal of Physiology—Renal Physiology, Jun. 2005, pp. F1084-F1089, vol. 288, No. 6.

Molitoris, Bruce A., Pharmacophotinics: Utilizing Multi-photon Microscopy to Quantify Drug Delivery and Intracellular Trafficking in the Kidney, Advanced Drug Delivery Reviews, Elsevier BV, Amsterdan, NL, Aug. 15, 2006, pp. 809-823, vol. 58, No. 7.

PCT International Search Report for PCT/US2006/014576 completed by the US searching Authority on Aug. 6, 2006.

Peti-Peterdi, Janos, Multiphoton Imaging of Renal Tissures in Vitro, American Journal of Physiology—Renal Physiology, Jun. 2005, pp. F1079-F1083, vol. 288, No. 6.

Prescott, L. F., S. Freestone and J. A. N. McAuslane, "Reassessment of the Single Intravenous Injection Method with inulin for Measurement of the Glomerular Filtration Rate in Man", Clin Sci (Lond), vol. 80, No. 2, 1991, pp. 167-176.

Qi, Z., I. Whitt, A. Mehta, J. Jin, M. Zhao, R. C. Harris, A. B. Fogo and M. D. Breyer, "Serial Determination of Glomerular Filtration Rate in Conscious Mice using FITC-Inulin Clearance", Am J. Physiol Renal Physiol, vol. 286, No. 3, 2004, pp. F590-F596.

Rabito, C. A., F. Panico, R. Rubin, N. Tolkoff-Rubin and R. Teplick, "Noninvasive, Real-Time Monitoring of Renal Function During Critical Care", J Am Soc Nephrol, vol. 4, No1. 7, 1994, pp. 1421-1428.

Rabito, C. A., R. H. Moore, C. Bougas and S. C. Dragotakes, "Noninvasive, Real-Time Monitoring of Renal Function: The Ambulatory Renal Monitor", J. Nucl Med, vol. 34, No. 2, 1993, pp. 199-207.

Rusinek, H., M. Kaur and V. S. Lee, "Renal Magnetic Resonance Imaging", Curr Opin Nephrol Hypertens, vol. 13, No. 6, 2004, pp. 667-673.

Sandoval, Ruben M. et al., Uptake and Trafficking of Fluorescent Conjugates of Folic Acid in Intact Kidney Determined Using Intravital Two-photon Microscopy, American Journal of Physiology—Cell Physiology, Apr. 21, 2004, pp. C517-0526, vol. 287, No. 2.

Sapirstein, L. A., M. R. Herrold, M. Janakis and E. Ogden, "Validity of Values for Glomerular Filtration Rate and Extracellular Fluid Obtained From Plasma Concentration-Time Decay Curves After Single Injections of Mannitol in the Dog", Am J. Physiol, vol. 171, No. 2, 1952, pp. 487-491.

Sturgeon, C., A. D. Sam, $2^{nd}$ and W. R. Law, "Rapid Determination of Glomerular Filtration Rate by Single-Bolus Inulin: A Comparison of Estimation Analyses", J Appl Physiol, vol. 84, No. 6, 1998, pp. 2154-2162.

Supplemental European Search Report, European Application No. 06750582, May 27, 2011, 10 pages.

Sutton, Timothy A. et al., Minocycline Reduces Renal Microvascular Leakage in a Rat Model of Ischemic Renal Injury, American Journal of Physiology q—Renal Physiology, Jan. 2005, pp. F91-F97, vol. 288, No. 1.

Wholohan, T., N. E. Yesberg and R. B. Cross, "Comparison of a Single-Injection Technique and Inulin Clearance for Determining Glomerular Filtration Rate in the Sheep", Exp Physiol, vol. 76, No. 2, 1991, pp. 289-291.

Yu, Weiming et al., Quantitative Intravital Microscopy Using a Generalized Polarity Concept for Kidney Studies, American Journal of Physiology—Cell Physiology, Nov. 2005, pp. C1197-C1208, vol. 289, No. 5.

Yu, Weiming, Rapid Determination of Renal Filtration Using an Optical Ratiometric Imaging Approach, American Journal of Physiology—Renal Physiology, Jun. 2007, pp. F1873-F1880, vol. 292, No. 6.

METHOD AND APPARATUS FOR KIDNEY FUNCTION ANALYSIS

This patent application is a divisional application of U.S. application Ser. No. 13/709,242, which was filed on Dec. 10, 2012, which is a divisional application of U.S. application Ser. No. 11/911,895, which is a U.S. national application under 37 C.F.R. 371(b) of PCT International Application Serial No. PCT/US2006/14576, which was filed on Apr. 18, 2006, and which claims priority to and the benefit of U.S. Provisional Patent Application Ser. No. 60/672,708 entitled "Method and Apparatus For Kidney Function Analysis," which was filed on Apr. 19, 2005, the entirety of which is expressly incorporated herein by reference.

BACKGROUND OF THE INVENTION

The present disclosure relates generally to methods and apparatuses for organ diagnostics, and more particularly to methods and apparatuses for kidney diagnostics.

Measurement of kidney functions is an important step in the diagnosis and treatment of kidney diseases. One such measure of kidney function is the Glomerular Filtration Rate (GFR). GFR is defined as the volume of blood (blood plasma) filtered by the kidney within a given time and is typically measured in milliliters per minute (ml/min). The typical clinical method used to measure GFR is the measurement of urine creatinine clearance. Creatinine is a metabolic product of the body. However, the GFR estimated by measuring creatinine level in the urine is only an estimate and not a direct measure of the actual GFR. This is because creatinine is produced by the body constantly and secreted into the urine in addition to filtration. Typical GFR measurements take at least 6 hours to 24 hours to complete. However, GFR measurements may not be possible when serum creatinine levels are not in equilibrium such as during acute renal failure. Typical GFR measurement techniques require collecting urine samples and/or drawing blood samples.

There are many diseases that affect the kidney or functions of the kidney. Proteinuria is a marker of chronic disease. An animal (e.g., a human patient) with proteinuria may develop renal failure, and early detection of proteinuria is beneficial in the treatment of many underlying diseases. The typical diagnostic method for proteinuria is the measurement of the albumin level in the urine. Such measurement is typically done semi-quantitatively using urine dip sticks or by chemically measuring the urinary protein to creatine ratio. Quantitative analysis typically requires a 24-hour urine collection. However, even 24-hour urine collection may result in a delayed diagnosis because of protein removal from the urine by proximal tubule cell reabsorption. For example, proteins may pass through the glomerulus (kidney filtration barrier), enter into the renal filtrate, and be reabsorbed by the renal tubular cells leaving little to no proteins in the urine. This may be of particular concern in diabetic nephropathy when the earliest detection of an altered glomerular permeability to protein is crucial for institution of therapy.

Blood and urine glucose levels are also used as diagnostic measurement. Abnormal blood glucose levels are directly related to diabetes and other diseases. Typical methods used to determine blood and urine glucose levels require the drawing of blood and/or the measurement of glucose content in the urine. These methods are relatively slow and do not allow real time monitoring of blood glucose levels.

Further, in many applications, it is desirable to know the pharmacokinetics of a drug. Typical methods used to measure drug pharmacokinetics require the drawing of blood from an animal (e.g., a human patient) which can be painful and slow. Other methods used to measure drug pharmacokinetics include the use of heavy and expensive medical imaging devices such as MRI.

SUMMARY OF THE INVENTION

The present invention comprises one or more of the features recited in the appended claims and/or the following features which, alone or in any combination, may comprise patentable subject matter:

A method for determining a physiological diagnostic of an animal is provided. The method may include the step of injecting a mixture of a number of first molecules and a number of second molecules into the animal. The molecular weight of the second molecule may be greater than the first molecule. The first and second molecules may be fluorescent probes. The method may also include the step of determining a molecular ratio of the first molecules and the second molecules. The molecular ratio may be a fluorescent intensity ratio of the first and second molecules. The method may further include determining physiological data. The physiological data may be, for example, a plasma clearance rate constant of a drug or chemical compound, a glomerular filtration rate, a filtration resistance, a clearance rate of glucose, a filtration resistance value of glucose, a glucose metabolic rate, and/or a drug metabolic rate. The glucose or drug metabolic rate may be determined based on the clearance rate of the glucose or drug and the filtration resistance value of glucose or of the drug, respectively.

An apparatus for determining a physiological diagnostic of an animal is also provided. The apparatus may include a number of finger receiving apertures. The apparatus may also include a number of light sources and a number of associated light receivers. Each of the number of light sources and associated light receivers may be associated with one of the number of finger receiving apertures. The light sources may be light-emitting diodes, lasers, diode lasers, and/or white light sources coupled with wavelength selection optics. The apparatus may further include a light generation circuit coupled to the number of light sources and a light detection circuit coupled to the number of associated light receivers. The light generation circuit may include a digital-to-analog converter circuit. The light detection circuit may be configured to detect a number of optical signals from the light receivers. The light detection circuit may also include a number of amplifiers and/or a number of filters. The apparatus may additionally include a photon pulse counting circuit. The photon pulse counting circuit may use TTL for digital signal detection. The pulse counting circuit may be coupled to the light detection circuit. The pulse counting circuit may be configured to determine a physiological diagnostic value based on the number of optical signals. Alternatively, in some embodiments, an analog-to-digital converter circuit may be used and configured for analog signal detection. The apparatus may yet further include a user interface electrically coupled to the pulse counting circuit. The user interface may include a display screen for displaying the physiological diagnostic value. The pulse counting circuit (or an analog-to-digital converter circuit) may be wirelessly communicatively coupled to the light detection circuit. Further, the light generation circuit, the pulse counting circuit, or analog-to-digital converter circuit, and the user interface may form portions of a personal computer.

The above and other features of the present disclosure, which alone or in any combination may comprise patentable subject matter, will become apparent from the following description and the attached drawings.

BRIEF DESCRIPTION OF THE DRAWINGS

The detailed description particularly refers to the following figures, in which.

DETAILED DESCRIPTION OF THE DRAWINGS

While the concepts of the present disclosure are susceptible to various modifications and alternative forms, specific exemplary embodiments thereof have been shown by way of examples in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the disclosure.

Figure 1:
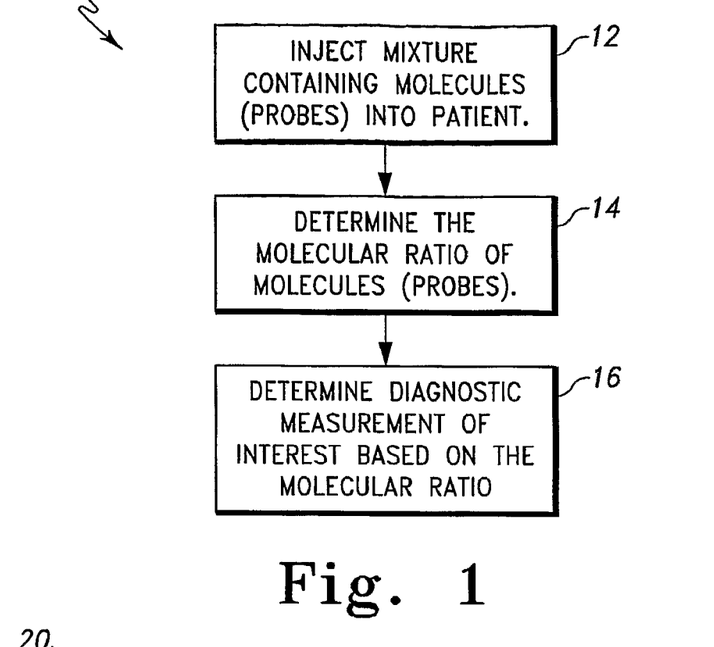
FIG. 1 is a process flow diagram of an algorithm for determining a kidney diagnostic.

Referring to FIG. 1, an algorithm 10 for determining physiological data, such as kidney diagnostic data, is shown. The algorithm 10 may be used to determine the Glomerular Filtration Rate of the kidneys, the molecular filtration resistance of a molecule and/or particle with predetermined sizes, and other kidney diagnostic measurements. To do so, in process step 12, a mixture of two (or more) molecules, i.e. A & B (or more), are injected into a live animal. As used herein, the term "animal" is intended to include humans. The two (or more) molecules are of different sizes (i.e., different molecular weight). Molecules with large molecular weights (MW) are typically retained in the blood stream for a long period of time (hours to days) in animals (e.g., human patients) with relatively normal renal functions. If one of the two or more molecules is of a large molecular weight (e.g. molecule A >70 kilo Dalton), the filtration of the other molecule(s) (e.g., molecule B) can be monitored and the clearance rate of molecule B can be calculated based thereon.

In process step 14 the molecular ratio of the molecules is determined. The molecular ratio (or generalized polarity (GP)) of B/A, $R_{B/A}$, measured in the blood stream as a function of time is directly related to the relative filtration rates (clearance rates) of these molecules, A & B (or more). The signal that represents molecular ratio, $R_{B/A}$, includes any properties that can be measured from A and B and may be determined based on the following equation:

$$R_{B/A} = \frac{S_B}{S_A} \quad (1)$$

where, $S_A$ is any one of a number of types of signals measured from A and $S_B$ is any one of a number of types of signals measured from B. The types of signals, $S_A$ and $S_B$, may include, but are not limited to, fluorescent intensity, any scattering signal (Rayleigh scattering, Raman, coherent antistock scattering, etc) from incident light (at one or more wavelengths), fraction of fluorescence lifetimes (in this case, the ratio signal $R_{B/A}$ is a ratio between the fractional contribution of fluorescence lifetime from B and the fractional contribution of fluorescence lifetime from A), absorbance, and polarization. This ratio signal (between A and B or more) also includes any combinations between any types of signals from A and B, e.g. ratio between fluorescent signal from A and scattering signal from B. In addition, a ratio signal, $R_{B/A}=S_B$, may be used when $S_A=1$ (a stationary signal of A normalized to 1).

In process step 16 the kidney diagnostics of interest is determined based on the ratio of molecules. For example, the decay function of $R_{B/A}(t)$ (or GP(t)) after initial infusion of A, B (or more) mixture can be described with a mathematical model (equation):

$$R_{B/A}(t) = c + \sum_{i=1}^{N} a_i \exp(-k_i t) \quad (2)$$

where $R_{B/A}(t)$ is the molecular ratio of molecules B and A measured as function of time; N is the total number of exponential processes involved including any glomerular filtration process, distribution process of the probe molecules in the blood stream, non-specific loss of probe molecules in the body, etc; c is a constant; $a_i$ is a pre-exponential factor or an amplitude; and $k_i$ is the relative decay constant (or rate constant) of individual processes, respectively. The individual values of k may be determined by performing linear (or non-linear if desire) least square fitting of the time series $R_{B/A}(t)$ (or GP(t)).

Where only the glomerular filtration process is present, the decay function $R_{B/A}(t)$ is a single exponential:

$$R_{B/A}(t) = c + a \exp(-kt) \quad (3)$$

where $R_{B/A}(t)$ is the molecular ratio of molecules B and A measured as function of time, c is a constant and a is the pre-exponential factor or the amplitude and k is the relative decay constant (or rate constant). As described above, if molecule A has a large molecular weight (e.g., greater than about 70 kD) and, therefore, is retained the kidney, the concentration of the molecule A in the blood stream can be considered stationary. By performing linear (or non-linear if desire) least square fitting of the time series $R_{B/A}(t)$ (or GP(t)), the value of k can be determined. The rate constant k (of the glomerular filtration process) is directly related to the glomerular filtration rate (GFR) and the total blood plasma volume, $V_{plasma}$ and molecular resistance, $\xi$, according to the following relationship:

$$k = \xi \frac{GFR}{V_{plasma}} \quad (4)$$

The value of molecular filtration resistance ξ is a measure of how difficult a molecule can pass through the kidney. If a molecule (or substance) has ξ=1, the molecule (or substance) can freely pass through the kidney filtration barrier without resistance. If a molecule (or substance) has ξ<1, the molecule (or substance) cannot freely pass through the kidney filtration barrier. If a molecule (or substance) has ξ=1, the molecule (or substance) is actively passing through (due to existence of active transportation mechanisms) the kidney filtration barrier.

Figure 5:
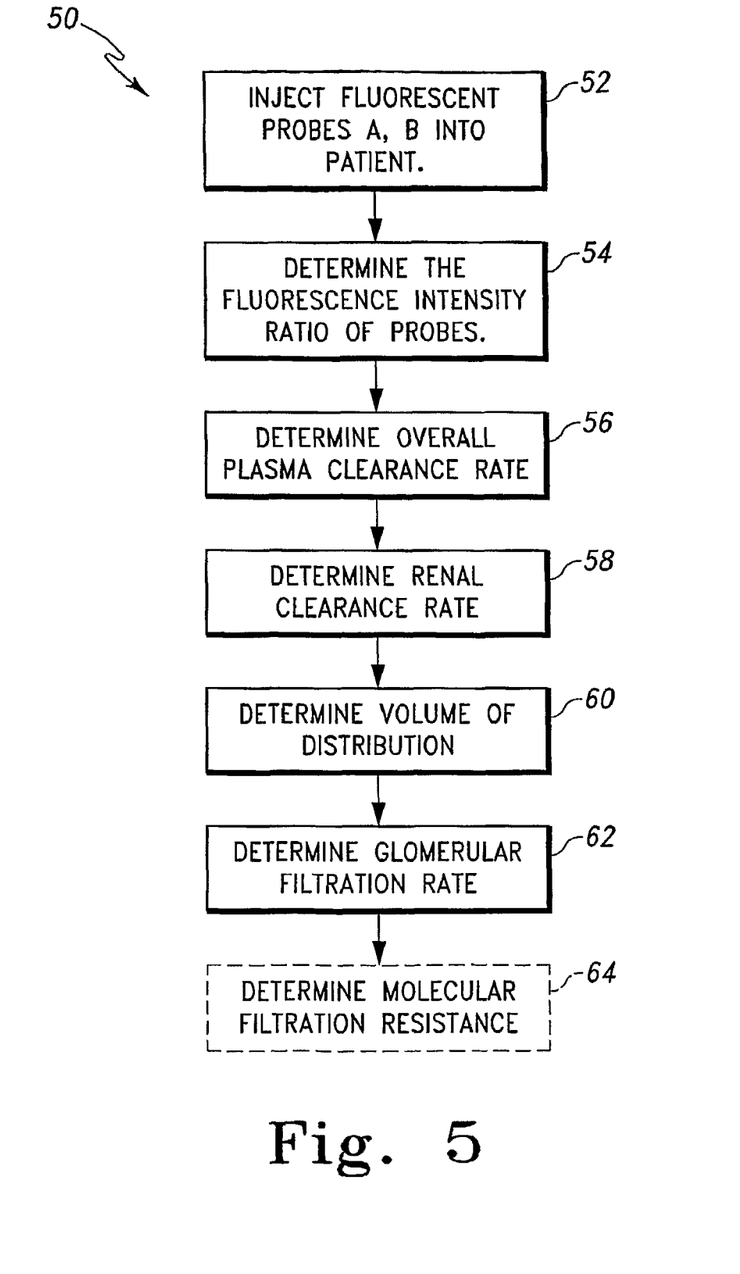
FIG. 5 is a process flow diagram of an embodiment of an algorithm for determining a Glomerular Filtration Rate of a kidney using a calculated volume of distribution.

The plasma volume, $V_{plasma}$, is proportional to the body weight $W_b$ and they have the following relationship:

$$V_{plasma} = \rho(\eta W_b) \quad (5)$$

where η is a weight-whole blood (including both plasma and blood cells) volume factor and ρ is a percentage factor of blood plasma volume from the whole blood volume. Average values of ρ and η of human are known or can be measured. In other embodiments, other methods of determining the plasma volume, $V_{plasma}$, may be used. For example, $V_{plasma}$ may be determined using any one or more of the determination procedures and/or equations discussed in detail below in regard to process step 60 of algorithm 50, which is illustrated in FIG. 5.

Accordingly, based on the molecular ratio as determined by equation 1 described above, kidney GFR and molecular filtration resistance ξ, may be determined for any molecules (or substances) using one or more of the equations 2-5 as described above.

In the following discussion of the decay constant k, molecular filtration rate, clearance rate, and rate constant are used synonymously. The relative molecular separation between molecule A and molecule B may be quantified using the Generalized Polarity based on the following equation:

$$GP = \frac{I_{A(large)} - I_{B(small)}}{I_{A(large)} + I_{B(small)}} \quad (6)$$

where $I_{A(large)}$ is the signal from the larger molecule and $I_{B(small)}$ is the signal from the smaller molecule. GP=1, when there is only signal from the larger molecule (only molecule A is present), and GP=−1 when there is only signal from the smaller molecule (only molecule B is present).

Alternatively, GP can also be defined as GP=($I_{B(small)}$−$I_{A(large)}$)/($I_{A(large)}$+$I_{B(small)}$). For the purpose of convention and discussion, the definition of GP in Equation 6 is used, but other definitions of GP may be used in other embodiments. The GP value can be used for quantification of the relative strength (namely the polarity of relative occupation of molecule A and molecule B) of the two individual signals from molecule A and B, respectively.

It should be appreciated that algorithm 10 may be used to determine any one of a number of kidney diagnostics. For example, referring now to FIG. 2, an algorithm 20 for determining a Glomerular Filtration Rate of a kidney is shown. Algorithm 20 includes process step 22 in which a mixture of two fluorescent probes (A and B) dissolved in saline or other aqueous solutions is injected into the blood stream of an animal. The fluorescent probes are of different sizes. For example, one of the fluorescent probes (e.g., probe A) may have a molecular weight (WM) of larger than 70 kD such as a 70 kD or a 500 kD fluorescent labeled dextran. The fluorescent signal from probe A is used as the reference signal. The other fluorescent probe (probe B) has smaller molecular weight that is not metabolized in the body. For example, fluorescent probe B may be small fluorescent molecules such as fluorescein, cascade blue, fluorescently labeled inulin, or other none toxic compounds.

Figure 2:
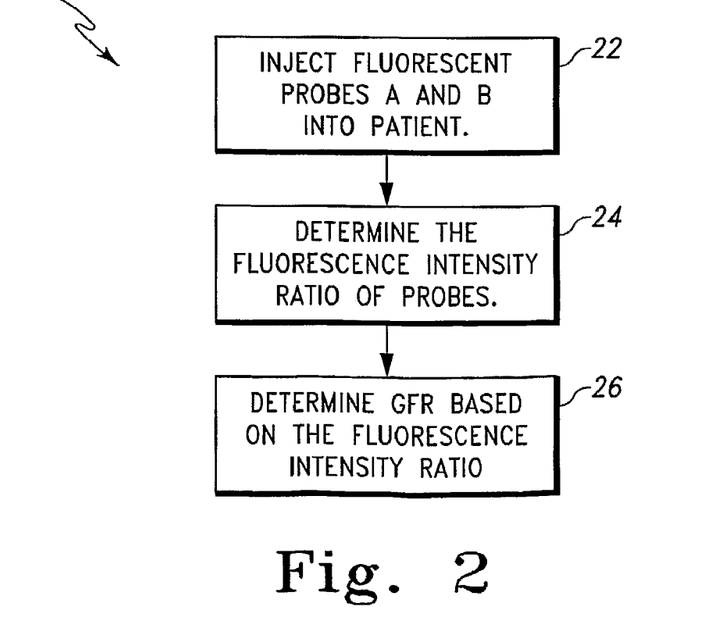
FIG. 2 is a process flow diagram of an embodiment of the algorithm of FIG. 1 for determining a Glomerular Filtration Rate of a kidney.

In process step 24, the fluorescence intensity ratio for the injected probes is determined. The fluorescence intensity ratio may be determined according to the equation: $R_{B/A}(t) = I_B(t)/I_A(t)$, where $I_B(t)$ and $I_A(t)$ are fluorescence intensities of the molecules B and A measured as functions of time, respectively. The fluorescence intensity ratio is measured from the blood stream (blood vessel/vessels) as a function of time after initial dye mixture injection. In process step 26, the GFR is calculated using the above-described equations 1-5 and least square fittings, assuming ξ for the smaller probe molecule is close to unity (ξ=1).

Additionally, algorithm 10 may be used as a diagnostic measure for Proteinuria. For example, referring to FIG. 3, an algorithm 30 for determining a protein filtration resistance as a diagnostic measurement for Proteinuria is shown. Algorithm 30 includes a process step 32 in which a mixture of three fluorescent probes (A, B and C) dissolved in saline or other aqueous solutions is injected into the blood stream. Probes A and B are analogous to A and B described above in regard to algorithm 20. Probe C is a fluorescently labeled protein (the marker protein) of any kind (globular or non-globular proteins), for example, a Texas-Red or FITC (fluorescein isothiocyanate) conjugated albumin.

Figure 3:
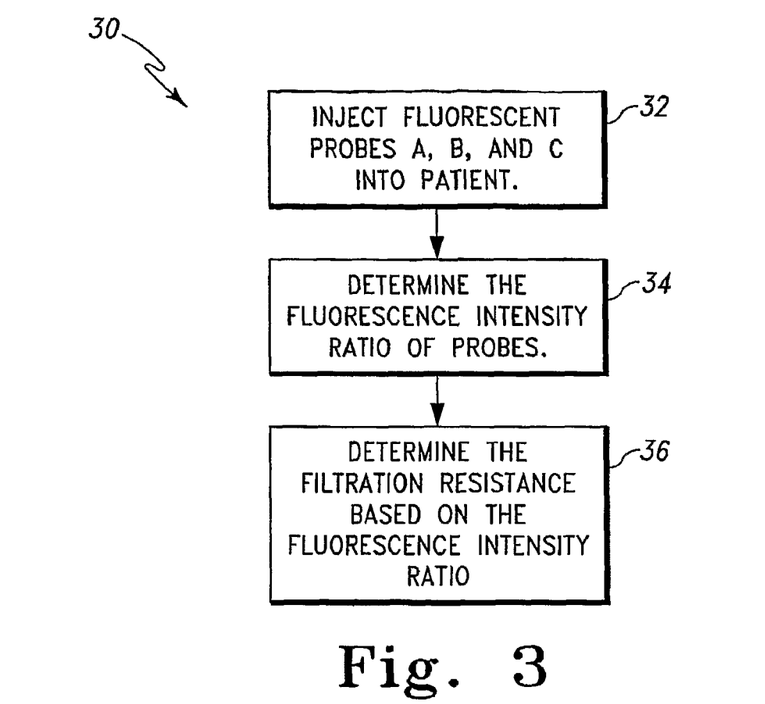
FIG. 3 is a process flow diagram of an embodiment of the algorithm of FIG. 1 for determining a protein filtration resistance.

In process step 34, the fluorescent signals from probes A, B and C in the blood vessels are recorded as functions of time. By performing least square fit of the fluorescence intensity ratio, $R_{B/A}(t) = I_B(t)/I_A(t)$, using the above-described equation 2 or 3, the rate constant $k_1$ of probe B may be determined. Similarly, by fitting the intensity ratio, $R_{C/A}(t) = I_C(t)/I_A(t)$, the rate constant $k_2$ of C (the protein) can be determined. In process step 36, the filtration resistance is determined. The relative filtration resistance $\xi_{C/B}$ may be calculated directly according to the following equation:

$$\xi_{C/B} = \frac{k_2}{k_1} \quad (7)$$

If $\xi_B$=1, the relative filtration resistance $\xi_{C/B}$=$\xi_C$ (filtration resistance of the marker protein).

The filtration resistance may be used as an indicator of the difficulty levels of the marker protein to pass through the kidney filtration barrier. A smaller value of $\xi_C$ indicates a greater difficulty level for the protein to pass through the kidney filtration barrier. This property of protein filtration resistance ξ can be used to diagnose Proteinuria. If an animal (e.g., a human patient) has a filtration resistance (of the marker protein) value larger than the average protein filtration resistance value from healthy individuals patient $\xi_{patient} > \xi_{average}$, it is likely the animal has developed Proteinuria.

In an alternative embodiment, the protein filtration resistance may be determined using two separate injections and associated measurements. In the first injection and measurement step, a mixture including only probes A and B is injected and the rate constant $k_1$ is determined thereafter. Subsequently, a mixture including only probes A and C is injected and the rate constant $k_2$ is determined thereafter.

Additionally, algorithm 10 may be used as a diagnostic measure for blood glucose. For example, referring to FIG. 4, an algorithm 40 for determining a blood glucose clearance rate and metabolic rate is shown. Algorithm 40 includes a process step 42 in which a mixture of three fluorescent probes (A, B and C1) dissolved in saline or other aqueous solutions is injected to the blood stream. Probes A and B are analogous to A and B described above in regard to algorithm 20. Probe C1 is a fluorescent glucose analog (L-glucose) where the glucose has a left-hand chirality (Levo-glucose in latin). L-glucose is not sweet and not metabolized by the body. In process step 44, the clearance rate $k_f$ and the filtration resistance $\xi_f$ of glucose (obtained from L-glucose) are determined. The clearance rate $k_f$ and the filtration resistance $\xi_f$ of glucose may be determined by using algorithm 30 described above in regard to FIG. 3.

Figure 4:
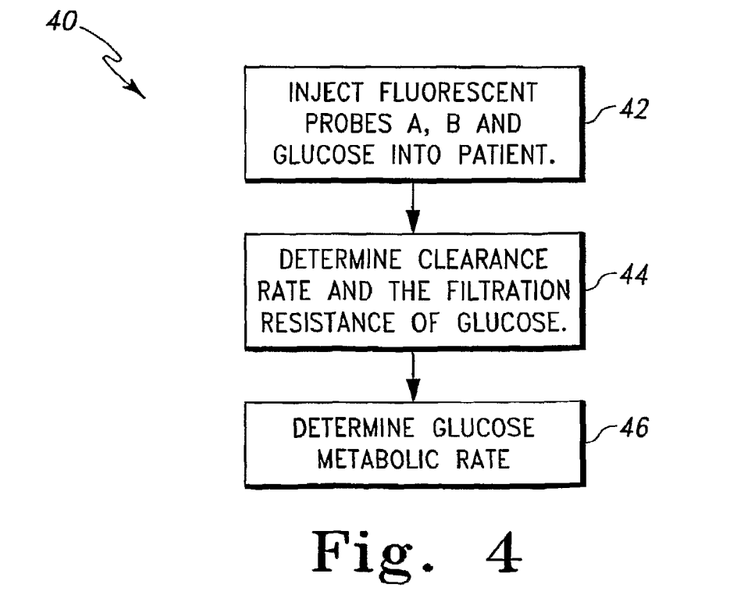
FIG. 4 is a process flow diagram of an embodiment of the algorithm of FIG. 1 for determining a blood glucose clearance rate and metabolic rate.

In process step 44, the glucose metabolic rate is determined. For D-glucose (Dextro-glucose, having a right-hand chirality), the body will metabolize this glucose as well as clear (filter) it from the blood. If a mixture of three fluorescent probes (A, B and C2) with C2 being a fluorescent glucose analog, such as 2-NBDG [2-(N-(7-nitrobenz-2-oxa-1,3-diazol-4-yl)amino)-2-deoxyglucose] or 6-NBDG, where the glucose has a right-hand chirality, the fluorescence intensity ratio $R_{C2/A}(t)=I_{C2}(t)/I_A(t)$ measured as function of time can be determined based on the following equation:

$$R_{C2/A}(t)=c+a\exp(-k_f t)+M(k_m,t) \quad (8)$$

where $k_f$ is the glucose filtration rate solely due to filtration, and $M(k_m,t)$ is a function describing the kinetics of glucose metabolism, and $k_m$ is the glucose metabolic rate. $k_f$ is known from process step 42, described above, using L-glucose fluorescent analog. The glucose metabolic rate, $k_m$, may be determined in process step 44 by fitting the glucose metabolic function $M(k_m,t)$.

Alternatively, the glucose metabolic rate may be determined by using a single injection of fluorescent probe mixture (A, C1 and C2) with A being the larger fluorescent molecule (>70 kD dextran), C1 being the L-glucose fluorescent analog, and C2 being D-glucose fluorescent analog. The glucose metabolic function may then be determined based on the following equation:

$$M(k_m, t) = R_{C2/A}(t) - R_{C1/A}(t) = \frac{I_{C2}(t) - I_{C1}(t)}{I_A(t)} \quad (9)$$

Further, algorithm 10 may be used to determine a drug clearance rate and/or metabolic rate. For example, the pharmacokinetics of metabolic and non-metabolic drugs may be monitored and measured using the algorithm 30 described above in regard to FIG. 3. For non-metabolic drugs (wherein only the clearance rate of the drug is considered), C1 from the fluorescent probe mixture (A, B and C1) described above in regard to algorithm 30 is replaced with a drug compound in order to measure this drug's clearance rate k and filtration resistance $\xi$. For a metabolic drug, the algorithm 40 described above in regard to FIG. 4 may be used by replacing the glucose with a respective drug compound to determine its clearance rate and the metabolic rate.

It should be appreciated that the determination of the glomerular filtration rate (GFR) of the kidneys, and the molecular filtration resistance of a molecule if desired, may be improved by accounting for non-renal clearance mechanisms (i.e., accounting for the non-renal clearance portion of k of equation 3 above). In addition, such determinations may be improved by calculating the distribution volume, $V_D$, of the animal (e.g., a human patient) being tested rather than basing the distribution volume on average values as discussed above in regard to equation 5. To do so, an algorithm 50 for determining a glomerular filtration rate of a kidney may be used as illustrated in FIG. 5.

The algorithm 50 begins with process step 52 in which a mixture of two fluorescent probes (A and B) dissolved in saline or other aqueous solutions is injected into the blood stream of an animal. The fluorescent probes are of different sizes. For example, one of the fluorescent probes (e.g., probe A) may have a molecular weight (WM) of larger than 70 kD such as a 70 kD or a 500 kD fluorescent labeled dextran. The fluorescent signal from probe A is used as the reference signal. The other fluorescent probe (probe B) has smaller molecular weight that is not metabolized in the body. For example, fluorescent probe B may be small fluorescent molecules such as fluorescein, cascade blue, fluorescently labeled inulin, or other none toxic compounds.

In process step 54, the fluorescence intensity ratio for the injected probes is determined. The fluorescence intensity ratio may be determined according to the equation:

$$R_{B/A}(t)=I_B(t)/I_A(t) \quad (10)$$

where $I_B(t)$ and $I_A(t)$ are fluorescence intensities of the molecules B and A measured as functions of time, respectively. The fluorescence intensity ratio is measured from the blood stream (blood vessel/vessels) as a function of time after initial dye mixture injection. The fluorescence intensity ratio may be determined using any suitable imaging analysis apparatus. For example, in one particular embodiment, the apparatus 100 illustrated in and described below in regard to FIGS. 6-9 may be used.

Alternatively, in another embodiment, the intensity ratio may be determined by first generating microvasular images of the kidney using a two-photon laser scanning fluorescence microscope system such as a MRC-1024P microscope, commercially available from Bio-Rad Laboratories of Hercules, Calif., equipped with a Nikon Diaphot inverted microscope, which is commercially available from Fryer Company Incorporated of Huntley, Ill., and external detectors (e.g., a 440-470 nm, a 500-550 nm, and a 560-650 nm detectors). Subsequently, the images may be analyzed to determine the fluorescence intensity ratio using any suitable imaging analysis system. For example, in one particular embodiment, the images may be analyzed to determine the fluorescence intensity ratio using Meta Imagining Series Version 6 software, which is commercially available from Universal Imaging Corporation of West Chester, Pa. To do so, the threshold level of each detection channel (i.e., each detector) may be set acceding to the average pixel value of an area of the image without significant autofluorescence from images taken before dye infusion. The average pixel values of the intensity ratio, R, from a region of interest may then be exported into an data analysis and plotting program such as PSI-PLOT Version 6, which is commercially available from Poly Software International of Pearl River, N.Y., for analysis.

Once the fluorescence intensity ratio has been determined, the overall plasma clearance rate is determined in process step 56. As discussed above in regard to equation 3, when only the glomerular filtration process is present, the decay function $R_{B/A}(t)$ is a single exponential time series. The overall plasma clearance rate may be determined by performing linear (or non-linear if desire) least square fitting of this single exponential time series. For example, the following decay function, $R_{vessel}(t)$, may be used:

$$R_{vessel}(t)=a\exp(-k_A t)+c \quad (11)$$

where $R_{vessel}(t)$ is the average pixel value of the intensity ratio from a given area (i.e., from a given blood vessel lumen region) extracted at different time points, a is the amplitude or the pre-exponential factor, c is a constant, t is time, and $k_A$ is the overall plasma clearance rate. As discussed above, the value of $k_A$ may be determined by performing nonlinear least square fitting on equation 11.

It should be appreciated that the overall plasma clearance rate, $k_A$, includes both the renal clearance rate, $k_A$, and the non-renal clearance rate (e.g., take up by the liver), $k_A$. As such, to improve the accuracy of calculations based on the clearance rate, such as determining the glomerular filtration rate and/or the molecular filtration resistance, the non-renal clearance rate may be subtracted from the overall plasma clearance rate or otherwise accounted for. To do so, the following equation may be used:

$$k_A = k_P + k_T \text{ or} \tag{12}$$

$$k_P = k_A - k_T \tag{13}$$

wherein $k_A$ is the overall plasma clearance rate, $k_P$ is the rate constant of the intrinsic plasma clearance (i.e., the renal clearance), and $k_T$ is the non-specific tissue distribution rate constant of a freely filtered molecule (i.e., the non-renal clearance). As discussed above, the value of $k_A$ may be determined using equation 11 and, in embodiments wherein the animal upon which the kidney analysis procedure is being performed is a non-human animal, the value of the non-specific tissue distribution rate constant, $k_T$, may be determined via a double whole kidney nephrectomy procedure. Because the value of the overall plasma clearance rate, $k_A$, and the value of the non-specific tissue distribution rate constant (i.e., the non-renal clearance rate), $k_T$, are known, the value of the rate constant of the intrinsic plasma clearance (i.e., the renal clearance rate), $k_P$, may be determined via the equation 13.

Alternatively, in embodiments wherein the animal upon which the kidney analysis procedure is being performed is a human patient, both the renal and non-renal clearance rates may be determined using multi-component models to account for individual kinetic processes. For example, the following equation may be used:

$$R_{B/A}(t) = c + a \exp(-k_{renal}t) + f(k_{non-renal}t) \tag{14}$$

wherein $R_{B/A}(t)$ is the intensity ratio, a and c are constants, t is time, $k_{renal}$ is the renal plasma clearance rate constant, f is a function including all kinetic processes that are not part of renal clearance (e.g., probe distribution, non-specific tissue absorption, etc.), and $k_{non-renal}$ is the non-renal plasma clearance rate constant. The clearance rates, $k_{renal}$ and $k_{non-renal}$, may be determined by performing a multi-component least square fitting procedure on equation 14. One of a number of different functions may be used to model the non-renal plasma clearance kinetics. For example, in some embodiments, a single exponential equation may be used as follows:

$$f(k_{non-renal}t) = b \exp(-k_{non-renal}t) \tag{15}$$

wherein b is a constant.

The accuracy of the determination of the renal and non-renal clearance rates may be improved by performing multiple tests on the human patient to determine multiple overall plasma clearance traces or values and subsequently performing a least square fitting of the multiple overall plasma clearance traces (i.e., performing a global fitting procedure on equation 14). For example, multiple clearance values or traces can be obtained by performing a number of tests using various concentration ratios of the marker molecules (e.g., molecules A and B). The average non-renal clearance, $k_{non-renal}$, may be then determined for an average human patient statistically based on the multiple tests. Subsequently, the renal plasma clearance rate constant, $k_{renal}$, may be determined directly using a single injection of the marker molecules (e.g., molecules A and B) based on the following equation:

$$k_{renal} = k_{overall} - k_{average\ non-renal} \tag{16}$$

wherein $k_{renal}$ is the renal plasma clearance rate constant, $k_{overall}$ is the average plasma clearance rate obtained by fitting the multiple clearance traces with a single exponential function, and $k_{average\ non-renal}$ is the average non-renal clearance rate.

In process step 60, the volume of distribution, $V_D$, is determined. Because at least one of the marker probes or molecules (e.g., probe/molecule A) is relatively large (e.g., a 500 kD fluorescent labeled dextran), this molecule or probe is not filtered by the kidney. As such, the volume of distribution, $V_D$, may be expressed as follows according to the conservation principle:

$$V_D = V_{before} * [C_{large}]_{before} / [C_{large}]_{plasma} \tag{17}$$

wherein $V_D$ is the volume of distribution (i.e., the plasma volume), $V_{before}$ is the volume of the large probe or molecule (e.g., the large dextran probe) before infusion into the patient, $[C_{large}]_{before}$ is the concentration of the large probe or molecule before infusion into the patient, and $[C_{large}]_{plasma}$ is the plasma concentration of the large probe or molecule after equilibrium has been obtained. Because the fluorescence intensity, $I_L$, of the larger probe or molecule (e.g., probe A) is proportional to its concentration, $[C_{large}]$, the volume of distribution (i.e., the plasma volume), $V_D$, may be determined as follows:

$$V_D = V_{before} * [I_L]before / [I_L]_{plasma} \tag{18}$$

wherein $V_D$ is the volume of distribution (i.e., the plasma volume), $V_{before}$ is the volume of the large probe or molecule (e.g., the large dextran probe) before infusion into the patient, $[I_L]_{before}$ is the total intensity values of the large probe or molecule measured before infusion, and $[I_L]_{plasma}$ is the total intensity values of the large probe or molecule measured after infusion. The value of volume of the large probe or molecule, $V_{before}$, is known and the value of $[I_L]_{plasma}$ may be determined from either the acquired time series images or using fluorescence spectroscopy measurement of drawn blood samples taken after a predetermined time (e.g., 10 minutes) to allow the plasma concentration to stabilize. For example the value of $[I_L]_{plasma}$ may be determined based on the average of three to five time, or more, time point measurements. The value of $[I_L]_{before}$ may be determined using the same instrument settings as used to determine the $[I_L]_{plasma}$.

In some embodiments, the volume of distribution (i.e., the plasma volume), $V_D$, may be determined based on body weight of the animal (e.g., a human patient) rather than the use of the equation 18 provided above. That is, the whole blood volume of the animal may be estimated as 5.5% of the total body weight. The total plasma volume, $V_D$, may then be estimated as 50% of the whole blood volume.

Although the process steps 56-60 are illustrated in FIG. 5 in a sequential order, it should be appreciated that the renal clearance rate and the volume of distribution may be determined in any order with respect to each other or contemporaneously with each other. For example, the volume of distribution may be determined prior to the determination of the renal clearance rate in some embodiments. In other embodiments, the volume of distribution may be determined contemporaneously with the determination of the renal clearance rate.

Once the renal clearance rate $k_p$ (or $k_{Renal}$) and that volume of distribution, $V_D$, have been determined in process steps 58 and 60, respectively, the glomerular filtration rate (GFR) may be determined in process step 62 based thereon. To do so, the following equation may be used:

$$GFR = k_P * V_D \quad (19)$$

wherein GFR is the glomerular filtration rate, $k_P$ is the rate constant of intrinsic plasma clearance (i.e., the renal clearance rate), and $V_D$ is the volume of distribution. As discussed above, the value of $k_P$ may be determined using equations 12-13 or 14-16 and the value of $V_D$ may be determined using the equations 17-18 or estimated as discussed above in detail.

In addition to the glomerular filtration rate, in some embodiments, the molecular filtration resistance may also be determined in process step 64. To do so, the following equation may be used.

$$\xi = k_{Pf}/k_P \quad (20)$$

wherein $\xi$ is the molecular filtration resistance, $k_{Pf}$ is the intrinsic plasma clearance rate (i.e., the intrinsic plasma clearance rate of the kidney), and $k_P$ is the plasma clearance rate of the large molecule or probe (e.g., probe A). Because the large size molecules typically do not freely pass through the glomerular filtration barrier, the clearance of the large size molecules from the blood will take a longer time than that of a freely filtered molecule. As such the molecular filtration rate can be used to determined the degree of glomerular injuries by using large molecules of varying sizes. Because molecular filtration resistance of smaller molecules (e.g., those molecules of a size sufficient to be freely filtered though the glomerular filtration barrier) may be substantially similar in kidneys having minor and severe glomerular damage, the smaller molecules are typically not used to determine the molecular filtration resistance.

In other embodiments, the molecular filtration resistance of the large molecule (e.g., molecules >20 kD), $\xi_{PLarge}$, may be determined using the following equation:

$$\xi_{PLarge} = \xi_{FITC\text{-}inulin} * [k_{AP(FITC\text{-}inulin)} - k_{TP(FITC\text{-}inulin)}] / [k_{APLarge} - k_{TPLarge}] \quad (21)$$

wherein $\xi_{PLarge}$ is the molecular filtration resistance of the large molecule (e.g., probe A), $\xi_{FITC\text{-}inulin}$ is the filtration resistance value of FITC-inulin measured from a group of control animals, $[k_{AP(FITC\text{-}inulin)} - k_{TP(FITC\text{-}inulin)}]$ is the plasma clearance rate of FITC-inulin measured from nephrosis animals at a given day after PAN treatment, and $[k_{APLarge} - k_{TPLarge}]$ is the clearance rate constant of the large molecule of interest (e.g., probe A). It should be appreciated that the value of the molecular filtration resistance, $\xi_{PLarge}$, may be compared with the corresponding values of measured urinary protein-to-creatinine ratio to determine the correlation between $\xi_{PLarge}$ and urinary protein secretion and the sensitivity of using the $\xi_{PLarge}$ value for early detection of proteinuria. It should be appreciated that in the above-described embodiment, FITC-inulin is used as a GFR marker (e.g., as molecule/probe B). However, in other embodiments, other types of GFR marker molecules/probes, such as other fluorescent or non-fluorescent marker molecules, may be used. In such embodiments, the equation 20 described above may be used to determine the molecular filtration resistance.

After injection of fluorescent probe mixture according to any of the embodiments described above, measurements may be performed using a multi-photon laser scanning fluorescence microscope. The location of microscopy measurements can be done any where on the body, for example, on the lips where the skin is relatively thin to allow easy observation of blood vessels. The fluorescence image of each of the injected fluorescent probes is subsequently acquired. The average intensity value from the blood vessel regions is calculated and plotted as functions of time. These intensity time series of these fluorescent probes are used for fitting and retrieving the corresponding k, $\xi$ and GFR.

However, other types of devices may be used to measure the fluorescence intensity from the blood stream of the animal. For example, existing instruments, such as instruments using optical coherent tomography or photon migration (diffusion) principles, may be adapted to perform the measurements.

Figures 6, 7:
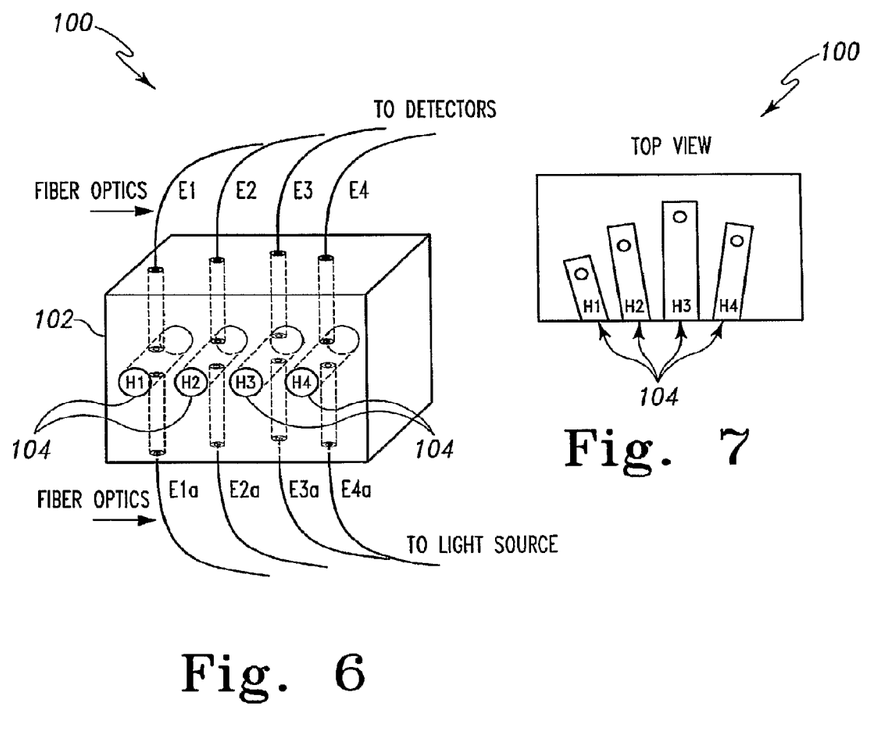
FIG. 6 is a perspective view of a measurement head of an apparatus for determining physiological diagnostics.
FIG. 7 is a top plan view of the measurement head of FIG. 6.

Referring now to FIG. 6, one embodiment of an apparatus 100 for determining physiological data related to an animal is shown. The physiological data may be used for a number of analysis purposes including diagnostics purposes such as kidney diagnostics, testing, drug research, drug development, and the like. Apparatus 100 allows non-invasive measurement of kidney functions, as well as other physiological functions, using optical signals. Apparatus 100 includes a measurement head 102 and a controller unit 120. The controller unit 120 is illustrated and described below in regard to FIG. 9. The measurement head 102 is illustratively designed to measure signals from the finger tips of human hands. However, in other embodiments, the measurement head 102 may be configured to measure signals from other body parts of a human patient and/or animal including, for example, from toes, ears, wrist, etc.

The measurement head 102 includes a number of finger receivers 104 designated as H1-H4. The finger receivers are configured to fit the anatomy of fingers from a human hand and may be embodied as cylindrical apertures. For example, as illustrated in FIG. 7, each of the finger receivers 104 extends at an angle, in respect to a vertical axis, to match the angle of the fingers of a human hand when the fingers are slightly separated. The measurement head 102 is made of a material that restricts ambient light from passing through the head 102. The measurement head 102 includes a number of source fiber optics, E1a-E4a, coupled to a respective number of light sources, L1-L4, of the controller unit (see FIG. 9). The source fiber optics, E1a-E4a, deliver an illumination light to the palm side of the finger tips. The measurement head 102 includes a number of receiver fiber optics, E1-E4, that collect optical signals generated by the source fiber optics, E1a-E4a. The receiver fiber optics, E1-E4, collect the optical signals from the opposite side of the finger tips (i.e., the side with finger nail). The contacts between the fiber optics, E1a-E4a and E1-E4, and the finger tips can be adjusted to assure good contact for illumination and optical signal detection. This can be accomplished by directly adjusting the fiber positions. In addition, the contact between the fiber optics and the finger nails can be improved by using a non-fluorescent coupling lubricant such as sucrose gel.

Figure 8:
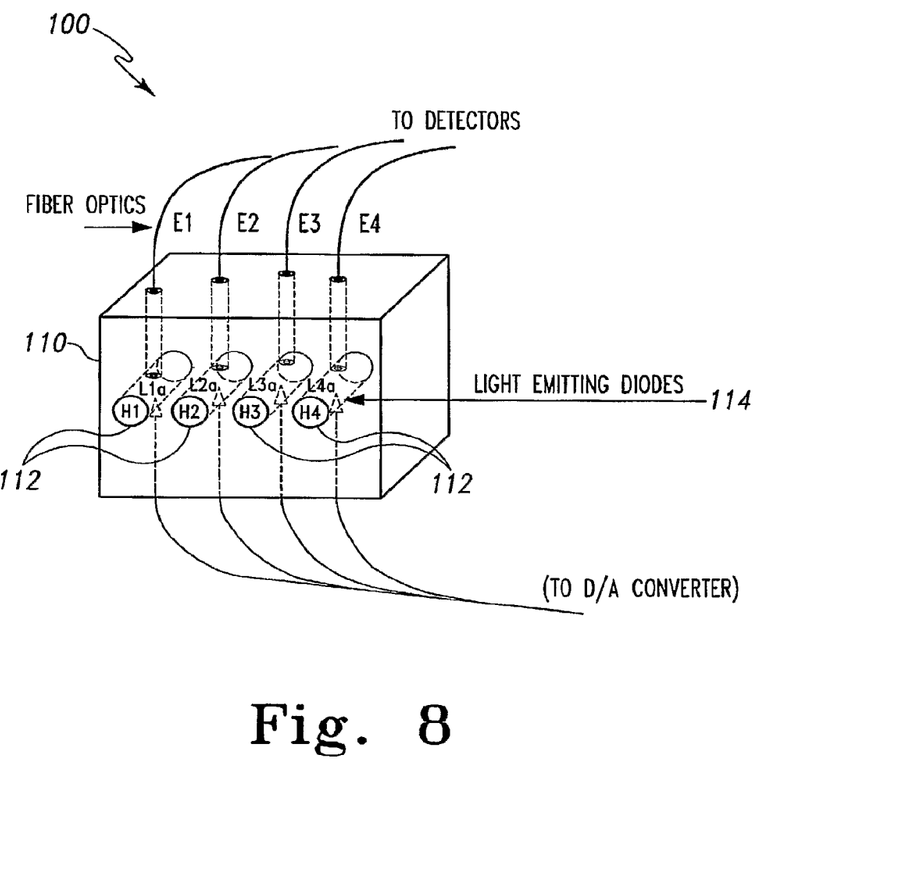
FIG. 8 is a perspective view of an alternative embodiment of the measurement head of FIG. 6.

Referring now to FIG. 8, in an alternative embodiment, apparatus 100 includes a measurement head 110 having a number of LEDs (light-emitting diodes) 114, L1a-L4a, as light sources. The light sources, L1a-L4a, are in contact with, or near contact with, the palm side of the finger tips when the animal's (e.g., human patient's) fingers are inserted into the finger receivers 112. Similar to measurement head 102, the measurement head 110 includes a number of receiver fiber optics, E1-E4, to collect the optical signals generated from the finger tips by illumination (excitation) from the light sources, L1a-L4a, respectively. The receiver fiber optics are positioned on the opposite side of the finger tips from the light sources (i.e., the side with finger nail). The intensity of the LEDs may be controlled by the controller 120 through digital-to-analog converters (D/A converters). Because the light sources, L1a-L4a, are located in the measurement head 110, loss of the illumination light is reduced.

Figure 9:
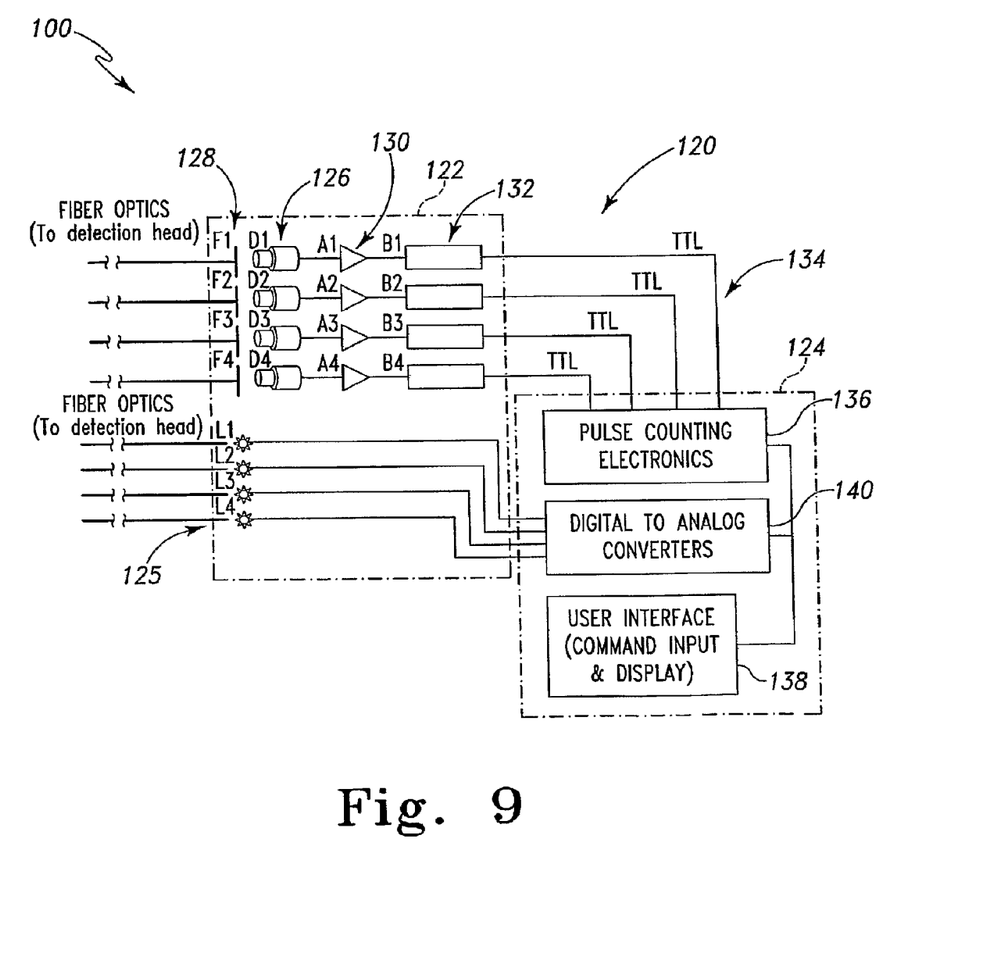
FIG. 9 is schematical illustration of a control unit of an apparatus for determining physiological diagnostics for use with the measurement head of FIG. 6 or FIG. 8.

The apparatus 100 also includes a controller unit 120. The controller unit 120 determines the physiological diagnostic via photon counting. Photon counting is typically used in applications requiring sensitive signal detection. In the illustrative embodiment, as illustrated in FIG. 9, the controller unit 120 includes an optical portion 122 and a control portion 124. In some embodiments, the optical portion 122 and the control portion 124 are integrated into a single portable unit. In other embodiments, optical portion 122 is integrated in a portable unit and the control portion 124 is included in a personal computer. It should be appreciated that the control portion 124 may be included in the personal computer as separate hardware devices, separate software algorithms, or a combination of hardware devices and software algorithms.

In embodiments including a measurement head 102, the optical portion 122 of the controller unit 120 includes a number of light sources 125, L1-L4, such as LEDs. The light sources 125 emit light at the same or different wavelengths. Fiber optics are coupled to the LEDs that deliver light to the measurement head 102. The optical portion 122 also includes a number of detectors 126, D1-D4. For the detection of fluorescence and other optical signals, the detectors may be embodied as photomultiplier tubes, photodiodes, CCD, or other device capable of detecting the fluorescence and other optical signals. The optical signals are delivered to the detectors through fiber optics that couple the measurement head 102 to the controller unit 120. In addition, the optic portion 122 includes a number of optical filters 128, F1-F4. The optical filters 128 filter the optical signals by rejecting or filtering noise and unwanted signals. The controller unit 120 also includes a number of amplifiers 130, A1-A4, that amplify the analog signals received from the detectors 126. The controller unit 120 includes a number of discriminators 132, B1-B4, that discriminate single photon pulses and generate output singles therefrom. Illustratively, the output signals are TTL (transistor-transistor logic) signals (so-called digital signal). However, it should be appreciated that in other embodiments, the discriminators 132 may generate other types of output signals.

The TTL signals generated by the discriminators 132 are transmitted to the control portion 124 via a number of communication links 134. The communication links 134 may be embodied as any type of communication link including discrete wires, PCB traces, or the like. Additionally, in other embodiments, the communication links 134 may be embodied as wireless communication links using any suitable wireless communication protocol such as, for example, Bluetooth. Once the output signals are received by the control portion 124, the output signals are processed by a pulse counting circuit 136 and further processed for display through a user interface 138 (e.g. a computer screen or a display panel on the controller unit). The control portion 124 also includes digital-to-analog converters (DAC) 140. The DACs 140 may be used to adjust the voltage levels of the LEDs and thereby control the illumination intensity. It should be noted that in embodiments wherein measurement head 110 is used, the light sources, L1a-L4a, are located in the measurement head 110 rather than the optic portion 122. As such, the light sources, L1a-L4a, are coupled directly to the DAC block 140 via a number of electrical interconnects, such as discrete wires. It should also be appreciated that although the illustrative embodiment includes only four light sources or source fiber optics and associated receiver fiber optics, other embodiments may include any number of light sources/source fiber optics and associated receiver fiber optics.

In an alternative embodiment, the digital signal acquisition and processing devices may be replaced with analog signal acquisition and processing devices. For example, the discriminators 132 may be removed or replaced with analog amplifiers and the pulse counting electronic circuit 136 may be replaced with analog-to-digital conversion circuitry. It should also be appreciated that although the illustrative embodiment includes only four light sources or source fiber optics and associated receiver fiber optics, other embodiments may include any number of light sources/source fiber optics and associated receiver fiber optics.

The light sources, L1a-L4a and L1-L4, may be embodied as LEDs, diode lasers, Xenon, arc lamps with appropriate filters, or other type of light source usable in the diagnostic measurement. The illumination wavelength used is selected according to the available fluorescent probes. For FITC-tagged molecules, an illumination at around 488 nm is used for the molecule excitation. A combination of blocking (blocking the 488 nm excitation light) and bandpass filters that allow passing through 500-550 nm light may be placed in front of the corresponding detector/detectors used for FITC fluorescence detection. In embodiments using scattering signal, the filter in front of the detector may allow the illumination light to pass through. Examples of configurations for the light sources, the filters, the fluorescent probes, and detectors are provided below in table 1.

TABLE 1

| Probes (fluorescent or non-fluorescent) | Light Sources (wavelength) | Filters (pass) | Detectors |
| --- | --- | --- | --- |
| Example 1 | | | |
| Cascade Blue-dextran | L1 (350-372 nm) | F1 (400-460 nm) | D1 (PMT) |
| FITC-dextran | L2 (465-490 nm) | F2 (500-550 nm) | D2 (PMT) |
| Texas Red-dextran | L3 (594 nm) | F3 (605-650 nm) | D3 (PMT) |
| Cy5-dextran | L4 (630-640 nm) | F4 (655-700 nm) | D4 (red sensitive PMT) |
| Example 2 | | | |
| FITC-dextran | L1 (465-490 nm) | F1 (500-550 nm) | D1 (PMT) |
| Texas Red-dextran | L2 (594 nm) | F2 (605-650 nm) | D2 (PMT) |
| Cy5-dextran | L3 (630-640 nm) | F3 (655-700 nm) | D3 (red sensitive PMT) |
| Scatter | L4 (735 nm) | F4 (725-745 nm) | D4 (red sensitive PMT) |

TABLE 1-continued

| Probes (fluorescent or non-fluorescent) | Light Sources (wavelength) | Filters (pass) | Detectors |
| --- | --- | --- | --- |
| Example 3 | | | |
| FITC-dextran | L1 (465-490 nm) | F1 (500-550 nm) | D1 (PMT) |
| Cy5-dextran | L3 (632 nm) | F3 (655-700 nm) | D3 (red sensitive PMT) |
| Scatter | L4 (632 nm) | F4 (620-650 nm) | D4 (red sensitive PMT) |

Accordingly, it should be appreciated that the apparatus 100 may be used in a number of applications for determining physiological diagnostics. For example, the apparatus 100 may be used to determine a glomerular filtration rate (GFR) for diagnosis of kidney function, determine a protein filtration resistance for diagnosis of Proteinuria and/or other diseases, determine a blood glucose clearance rate and/or glucose metabolic rate, and/or determine a drug clearance rate and/or drug metabolic rate. It should be appreciated that in some embodiments the apparatus 100 may include only one or a limited number of illumination channels and respective detection channels for a given application (e.g., GFR measurement using one fluorescent probe.).

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the methods and apparatuses described herein. It will be noted that alternative embodiments of the methods and apparatuses of the present disclosure may not include all of the features described yet still benefit from at least some of the advantages of such features. Those of ordinary skill in the art may readily devise their own implementations of the methods and apparatuses that incorporate one or more of the features of the present invention and fall within the spirit and scope of the present disclosure as defined by the appended claims.

The invention claimed is:

1. A method for determining physiological data of a single organ of an animal, the method comprising:
  injecting a number of a first molecule and a number of a second molecule into the animal, the second molecule having a greater molecular weight than the first molecule;
  determining a molecular ratio of the first molecule and the second molecule; and
  determining the physiological data of the single organ based on the molecular ratio.

2. The method of claim 1, wherein the injecting step includes injecting a mixture containing a number of the first molecule and a number of the second molecule into the animal.

3. The method of claim 1, wherein at least one of the first and the second molecules is a sugar with left-hand chirality.

4. The method of claim 1, wherein the first and second molecules are fluorescent probes.

5. The method of claim 4, wherein determining a molecular ratio includes determining a fluorescent intensity ratio of the first and second molecules.

6. The method of claim 1, wherein the molecular weight of the second molecular is greater than about 70 kilo-Daltons.

7. The method of claim 1, wherein the single organ is a kidney, and wherein determining the physiological data includes determining a glomerular filtration rate.

8. The method of claim 7, wherein the glomerular filtration rate is determined using the following equation:

$$GFR = \frac{V_{plasma}}{k * \xi}$$

wherein GFR is the glomerular filtration rate, $V_{plasma}$ is a total blood plasma volume, k is a clearance rate, and $\xi$ is a molecular filtration resistance.

9. The method of claim 8, wherein the clearance rate, k, is a renal clearance rate clearance.

10. The method of claim 9, wherein the renal clearance rate is determined using the following equation:

$$k_{renal} = k_{overall} - k_{average\ non-renal}$$

wherein $k_{renal}$ is the renal clearance rate, $k_{overall}$ is an average plasma clearance rate, and $k_{average\ non-renal}$ is an average non-renal clearance rate.

11. The method of claim 8, wherein the total blood plasma volume, $V_{plasma}$, is determined based on an average whole blood volume.

12. The method of claim 8, wherein the total blood plasma volume, $V_{plasma}$, is determined using the following equation:

$$V_D = V_{before} * [I_L]_{before} / [I_L]_{plasma}$$

wherein $V_D$ is the total blood plasma volume, $V_{before}$ is a volume of the second molecule prior to the injecting step, $[I_L]_{before}$ is a total fluorescent intensity value of the second molecule prior to the injecting step, and $[I_L]_{plasma}$ is a total fluorescent intensity value of the second molecule subsequent to the injecting step.

13. The method of claim 1, wherein determining the physiological data includes determining a molecular filtration resistance.

14. The method of claim 13, wherein the molecular filtration resistance is determined using the following equation:

$$\xi = k_{Pf} / k_P$$

wherein $\xi$ is the molecular filtration resistance, $k_{Pf}$ is an intrinsic plasma clearance rate, and $k_P$ is a plasma clearance rate of the second molecule.

15. The method of claim 1, wherein determining the physiological data includes determining a clearance rate of glucose.

16. The method of claim 15, wherein determining the physiological data further includes determining a filtration resistance value of glucose.

17. The method of claim 16, wherein determining the physiological data further includes determining a glucose metabolic rate based on the clearance rate of glucose and the filtration resistance value of glucose.

18. The method of claim 1, wherein determining the physiological data includes determining a clearance rate of a drug.

19. The method of claim 18, wherein determining the physiological data further includes determining a filtration resistance value of the drug.

20. The method of claim 19, wherein determining the physiological data further includes determining a drug metabolic rate based on the clearance rate of the drug and the filtration resistance value of the drug.

* * * * *